United States Patent [19]

Pittaro

[11] 4,134,081

[45] Jan. 9, 1979

[54] CLOCK CIRCUIT FOR USE IN PULSE-ECHO ULTRASONIC DEFECT TESTING

[75] Inventor: Richard J. Pittaro, Stamford, Conn.

[73] Assignee: Krautkramer-Branson, Incorporated, Stratford, Conn.

[21] Appl. No.: 843,451

[22] Filed: Oct. 19, 1977

Related U.S. Application Data

[62] Division of Ser. No. 764,343, Jan. 31, 1977, Pat. No. 4,064,742.

[51] Int. Cl.$^2$ .............................................. H03B 3/04
[52] U.S. Cl. .................................... 331/1 A; 331/14; 331/34; 331/153; 331/177 R
[58] Field of Search ..................... 331/1 A, 14, 18, 25, 331/34; 73/598, 602, 606, 609, 611, 614

[56] References Cited

U.S. PATENT DOCUMENTS

| 3,185,938 | 5/1965 | Pelosi | 331/14 X |
| 3,271,688 | 9/1966 | Gschwind et al. | 331/1 A X |

*Primary Examiner*—Siegfried H. Grimm
*Attorney, Agent, or Firm*—Ervin B. Steinberg; Philip J. Feig

[57] ABSTRACT

A clock circuit comprising a synchronizable voltage controlled oscillator in combination with a programmable address means, which address means is adjusted commensurate with the acoustic velocity of the workpiece, provides clock pulses from the oscillator having a stable and accurate acoustic velocity dependent frequency. An entrant surface responsive electrical signal responsive to an ultrasonic search signal entering the workpiece is also provided to the clock circuit for assuring that the clock pulses are synchronized with the receipt of the electrical signal.

4 Claims, 4 Drawing Figures

CLOCK CIRCUIT FOR USE IN PULSE-ECHO ULTRASONIC DEFECT TESTING

This is a division of application Ser. No. 764,343, filed Jan. 31, 1977 and now U.S. Pat. No. 4,064,742.

BRIEF SUMMARY OF THE INVENTION

This invention refers to an ultrasonic pulse-echo defect gate circuit exhibiting improved stability and calibration adaptability. More specifically, the invention concerns a synchronizable clock circuit used in generating a defect gate most suitable for use in ultrasonic pulse-echo immersion testing of workpieces.

In ultrasonic pulse-echo testing of workpieces for defects, it is sometimes desirable to test for defects disposed in a predetermined region of a workpiece. The general method of testing a workpiece for defects comprises the steps of transmitting an ultrasonic search signal into the workpiece and receiving echo responsive signals arising from the search pulse intercepting an acoustic discontinuity such as the entrant surface or a defect disposed in the workpiece. A defect gate is generated commensurate with the time interval echo responsive signals arising from acoustic discontinuities in the predetermined region of the workpiece are to be received. Only defects received during the defect gate time interval are processed.

Methods and apparatus for generating defect gates are well known in the art. Generally, the defect gate commences a predetermined time after receipt of an entrant surface echo responsive signal measured by counting the number of counts generated from a clock circuit after receipt of the entrant surface responsive signal. Unless the clock is synchronized to the entrant surface signal, an error of one count (jitter) will be manifest in the start of the defect gate. In order to overcome this error due to jitter when an accuracy in the order of 10 one-thousandths of an inch in an aluminum workpiece is desired, a clock having a frequency of approximately 100 megahertz is needed. Clocks at such a high frequency and the associated counting and logic circuits are generally of complex and expensive construction for maintaining stability over normal operating temperature ranges during extended test periods.

Moreover, when testing workpieces having different acoustic velocities, a plurality of such high frequency clock circuits, each oscillating at a different high frequency are required. In the case of a workpiece of a slightly different alloy, falling within the fixed frequencies, the start of the defect gate as well as the duration of the gate will be in error due to the incorrect clock frequency.

In order to overcome these prior difficulties, a clock circuit is described which is synchronized to the entrant surface responsive echo signal thereby obviating error due to jitter. Moreover, the described circuit includes address means for calibrating the clock frequency responsive to the acoustic velocity of any material to be tested. A defect gate is therefore generated commencing a predetermined time after receipt of the entrant surface responsive echo signal and having a predetermined duration. The clock used for generating such gate exhibits long term stability using a single variable frequency synchronized clock.

A principal object of the present invention is the provision of a highly stable programmable clock circuit for use in an ultrasonic pulse-echo immersion testing apparatus.

Another object of the invention is the provision of a clock circuit, programmable commensurate with the acoustic velocity of a workpiece, for use in generating a defect gate in an ultrasonic pulse-echo testing apparatus.

A further object of the invention is the provision of a highly stable programmed clock circuit for generating clock pulses synchronized to the entrant surface responsive echo signal and having a frequency commensurate with the acoustic velocity of the workpiece.

Further and still other objects of the invention will become more clearly apparent when the following description is read in conjunction with the accompanying drawings.

DETAILED DESCRIPTION OF THE INVENTION

Figure 1:
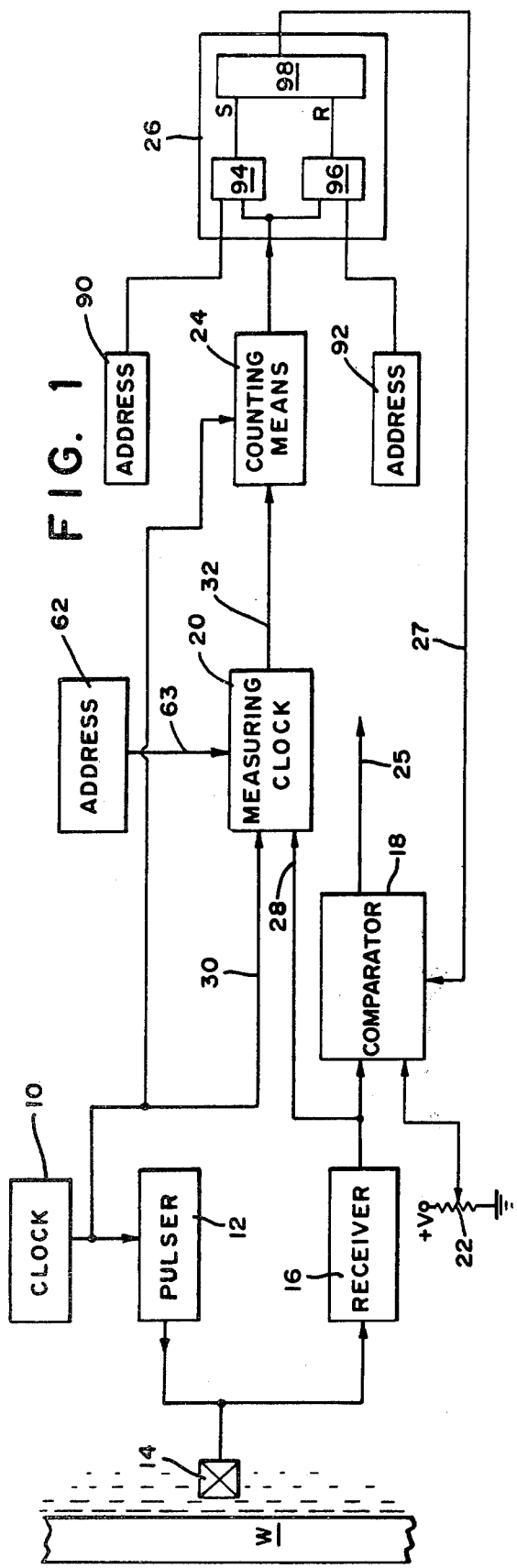
FIG. 1 is a schematic electrical block circuit diagram of a preferred embodiment of the invention.

Referring now to the figures and FIG. 1 in particular, there is shown a schematic block circuit diagram of a preferred embodiment of the invention. A repetition rate clock 10 provides trigger pulses, typically at a frequency in the range between 50 Hz and 20 kHz to a pulser 12 for cyclically energizing an electroacoustic transmit-receive probe 14. The transmit-receive probe 14 responsive to the electrical signals from the pulser 12 periodically transmits an ultrasonic search pulse through a water coupling path into a workpiece W which is to be examined for the presence of defects, and subsequently receives echo signals arising from acoustic discontinuities, such as the entrant surface or defects disposed in the workpiece. These echo signals are converted by the probe 14 to electrical echo responsive signals and fed to a receiver circuit 16 which provides echo responsive electrical signals to a comparator 18 and measuring clock circuit 20. Responsive to each respective search signal, an entrant surface responsive electrical signal is provided for synchronizing the measuring clock 20 and defect responsive electrical signals having an amplitude commensurate with the magnitude of the intercepted defect is provided to the comparator circuit 18.

The measuring clock 20 provides a train of clock pulses at a programmed frequency to a counting means 24. The counting means 24 provides a count signal to gate generator circuit 26 indicative of the quantity of clock pulses received by the counting means 24 after receipt of the trigger pulse from clock 10. A typical embodiment of gate generator circuit 26 is shown in FIG. 1.

Address 90 is programmed to a value equal to the initial depth of the workpiece measured from the entrant surfaces at which the defect gate is to commence and address 92 is programmed to a value equal to either the final depth of the workpiece region to be examined or to the dimension of the predetermined region. The difference of the two programmed values being equal to the width of the defect gate. Address 90 is coupled to one input of a comparator 94. The other input of comparator 94 receives the count signal from counting means 24. When the count signal equals the signal from address 90 an output signal along the S conductor from comparator 94 to flip-flop 98 sets the flip-flop 98. In a like manner, when the count signal from counting means 24 equals the signal from address 92 an output signal from a second comparator 96 along conductor R resets the flip-flop 98. The resulting gate at the output conductor of gate generator circuit 26 is fed via conductor 27 to the enable (strobe) input of a comparator 18 for enabling the comparator 18 only during the time interval that the defect gate is manifest along conductor 27.

Defect responsive electrical signals from receiver 16 are provided to one input of comparator 18. The other input of comparator 18 is coupled to a potentiometer 22 which provides a direct current voltage reference level to the comparator. One end of the potentiometer 22 is coupled to a power supply and the other end is coupled to ground potential. The comparator 18 will provide a defect present signal to a signal evaluation unit along output conductor 25 only when the following conditions are met: (1) the amplitude of the defect responsive electrical signal from receiver 16 exceeds the reference level as determined from potentiometer 22 and (2) the defect gate signal is manifest along conductor 27. Hence, only defect information concerning a defect exceeding a minimum magnitude disposed in the predetermined workpiece region of interest will be provided along conductor 25 for further evaluation and processing in a manner known in the art.

Figure 4:
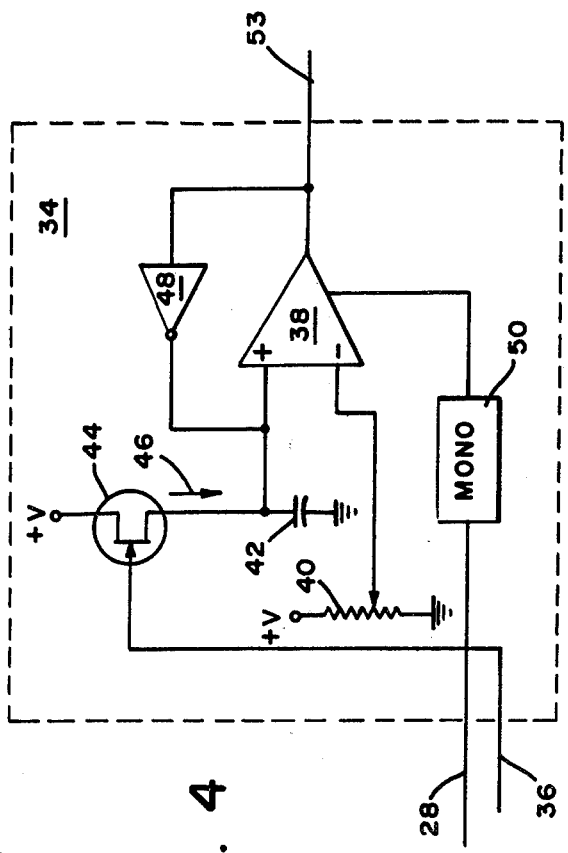
FIG. 4 is an electrical circuit diagram of an oscillator used in the embodiments shown.
Figure 2:
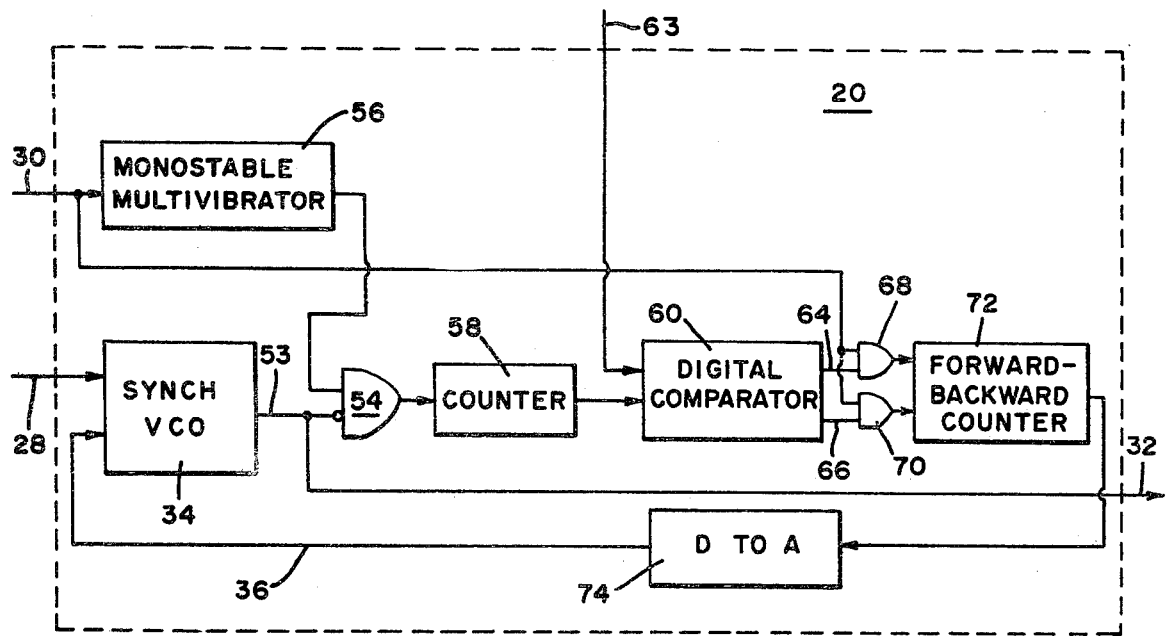
FIG. 2 is a schematic electrical block circuit diagram of a preferred embodiment of a portion of the circuit in FIG. 1.

The important feature of the present invention resides in the design and construction of the measuring clock circuit 20. In FIG. 2 a preferred embodiment of the measuring clock circuit 20 is shown. A synchronizable voltage controlled oscillator 34 provides clock pulses having the leading edge of the first pulse synchronized to the entrant surface responsive electrical signal from receiver 16 provided along conductor 28. The frequency of the clock pulses is responsive to the voltage provided along conductor 36. A typical oscillator 34 as shown in FIG. 4 includes a high speed comparator 38 (for instance, a type NE 521 comparator manufactured by Signetics Corporation) with the inverting input coupled to a predetermined voltage level provided from a potentiometer 40. The non-inverting input of the comparator 38 is connected to a ramp generator comprising a capacitor 42 connected between ground potential and a voltage controlled impedance device 44, the latter being connected between the non-inverting input of the comparator and the positive potential of a direct current power supply. In the present embodiment a field effect transistor 44 is provided for varying the current flow in the direction of arrow 46 charging the capacitor 42 responsive to the analog voltage signal provided along conductor 36. In alternative embodiments a voltage controlled current generator may replace the field effect transistor. An inverter 48 provides a delay between the output and the non-inverting input of comparator 38. A monostable multivibrator 50 is coupled for receiving the signal along conductor 28 and providing an enabling pulse to the comparator 38.

The output of monostable multivibrator 50 is normally in its low state for causing the output of comparator 38 to be in its high state. When the comparator 38 is in its normal high state, the output of inverter 48 is in its low state and the voltage between the non-inverting input of comparator 38 and ground potential is approximately zero volts. Responsive to the receipt by monostable multivibrator 50 of an entrant surface responsive electrical signal from receiver 16 along conductor 28, the output signal of the multivibrator 50 assumes its high state, thus providing an enabling pulse to comparator 38. Upon receipt of the enabling pulse, the output of comparator 38 assumes its low state causing the output of inverter 48 to try to assume its high state, resulting in the voltage between the non-inverting input of comparator 38 and ground potential (i.e., the voltage across capacitor 42) to increase. When the voltage across the capacitor 42 exceeds the predetermined level at the non-inverting input of comparator 38, the output of comparator 38 reassumes its high state. The voltage at the non-inverting input of the comparator 38 is returned to zero volts after a time delay caused by the inverter 48. The voltage across capacitor 42 then immediately begins to increase again. This cycle repeats itself for as long as the output of the monostable multivibrator 50 is in its high state. The enabling pulse pulse width is adjusted to commence with the receipt of the entrant surface responsive electrical signal and terminate prior to the transmission of the subsequent trigger pulse from clock 10.

It will be apparent that changes of the analog signal along conductor 36 cause a change in the current used to charge capacitor 42. The resulting change in the shape of the ramp voltage waveform across capacitor 42 affects the frequency of the pulses at the output of comparator 38. The pulses at the output of comparator 38 are provided along conductor 32 to counting means 24 for use in accurately measuring the distance from the entrant surface of a workpiece. It is essential therefore, that the frequency of the output pulses of comparator 38 exhibit stability over the operating period of the testing apparatus.

To this end, the output signal of oscillator 34 is provided via conductor 53 to a gated counter circuit comprising a gate circuit 54, a monostable multivibrator 56 and a counter 58 (see FIG. 2). The monostable multivibrator 56 is adjusted for providing a pulse to the gate circuit 54, such pulse having a predetermined pulse width, typically twenty microseconds, causing the opening of gate 54 for the duration of the fixed pulse width pulse. Counter 58 counts the quantity of pulses received from oscillator 34, passing through open gate 54, during the predetermined monostable multivibrator 56 pulse period. The count from counter 58 is provided to one input of a digital comparator 60. The other input of comparator 60 is coupled to an address means 62 via conductor 63 for receiving a predetermined programmed count commensurate with the acoustic velocity of the workpiece. The address means may be a thumbwheel switch, potentiometer, or the like.

The comparator 60 provides along a first output conductor 64 an output pulse when the signal from counter 58 exceeds the signal from address means 62 and provides along a second output conductor 66 an output pulse when the signal from address means 62 exceeds the signal from counter 58. The conductors 64 and 66 are each connected to one input of respective gates 68 and 70. The other inputs of the gates 68 and 70 are connected via conductor 30 to clock 10. Gate 68 output is connected to the count "down" input of forward-backward counter 72 and the gate 70 output is connected to the count "up" input of forward-backward counter 72. Upon each occurrence of the trigger signal from clock 10, the counter 72 counts "up" or "down" one count responsive to the output signals from comparator via gate 68 or gate 70. A digital to analog converter 74 converts the digital count signal at the output of forward-backward counter 72 into an analog signal. The analog signal is then provided along conductor 36 to the input of oscillator 34 for causing the frequency of the output pulses from oscillator 34 to change in the manner for causing the frequency to become equal to the programmed quantity adjusted by the address means 62.

The above cycle of events is repeated until the comparator 60 fails to provide an output pulse along either conductor 64 or conductor 66, thereby indicating that the oscillator frequency is equal to the programmed frequency.

It will be apparent that the oscillator 34 can be constructed from inexpensive components since the feedback loop described provides for a stable and accurate clock signal from oscillator 34. A deviation from the programmed frequency will cause the system to readjust the oscillator frequency. The oscillator 34 frequency is effectively checked with each trigger pulse.

In a modification of the described embodiment a go/no-go circuit may be coupled to the output of comparator 60 for providing a "go" signal when the comparator 60 output indicates that the oscillator is providing clock pulses at the programmed frequency and a "no-go" signal when the frequency differs from the programmed value.

For testing workpieces having a different acoustic velocity, the address means 62 is adjusted for calibrating the apparatus commensurate with the acoustic velocity. The address means 62 thus varies the measuring clock frequency in a simple manner commensurate with the acoustic velocity of the workpiece for providing an improved pulse-echo ultrasonic testing apparatus than known heretofore.

Figure 3:
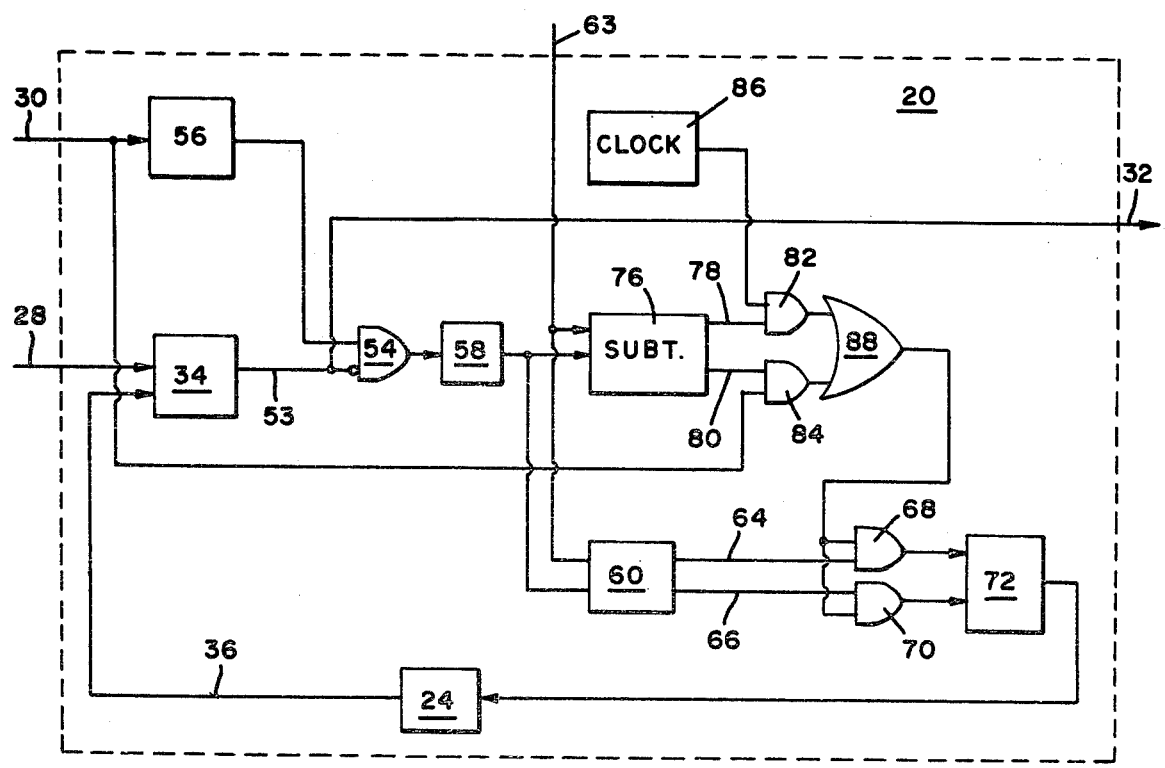
FIG. 3 is a schematic electrical block circuit diagram of an alternative embodiment of the circuit per FIG. 2.

In a further modification of the circuit as revealed in FIG. 3, a subtraction circuit 76 is coupled to the output of counter 58 and address means 62 via conductor 63. The subtraction circuit 76 provides a signal along conductor 78 to gate circuit 82 when the difference between the measured frequency and the programmed frequency exceeds a predetermined quantity and provides a signal along conductor 80 to gate 84 when the difference between the two signals is less than the predetermined quantity. A high frequency clock 86 provides pulses having a frequency much greater than the frequency of clock 10 to the other input of gate 82. Thus, when the signal along conductor 78 indicates that the frequency of oscillator 34 differs greatly from the programmed frequency, the forward-backward counter 72 changes its count at a greater rate than when the signal along conductor 80 indicates the frequency is close to the programmed frequency. An OR gate 88 couples either the clock pulses from clock 10 or the clock pulses from high frequency clock 86 to one input of each of the gates 68 and 70 for changing the count in forward-backward counter 72 in the same manner as described above.

OPERATION

In operation, the probe 14 is acoustically coupled via a coupling path of water or other suitable couplant to a workpiece W to be tested. The address means 62 is adjusted commensurate with the known acoustic velocity of the workpiece. As described, the feedback loop adjusts the frequency of the oscillator 34 until the number of pulses provided along conductor 53 during a twenty microsecond time interval is equal to the programmed count provided along conductor 63, which programmed count is commensurate with the acoustic velocity. Hence, the frequency of the clock pulses at the output of oscillator 34 is made commensurate with one twentieth of the acoustic velocity of the workpiece. The quantity of clock pulses counted by counting means 24 during the time corresponding to a search signal traversing the workpiece from the entrant surface to the rear wall is commensurate with 0.1 times the thickness of the workpiece. In practical terms, the frequency of the oscillator 34 is adjusted to the programmed count in a very short period of time and by virtue of the constant checking feature of the clock circuit 20, the frequency is maintained constant. Thus, after a very short delay, approximately one second, the apparatus is calibrated and measurement can begin. Alternatively, an alarm circuit of the type described above may be incorporated into the circuit for inhibiting any defect gate from gate generator circuit 26 until the oscillator 24 attains the desired frequency as indicated by the lack of an output signal from digital comparator 60.

A trigger pulse from clock 10 to pulser 12, causes the pulser 12 to provide a trigger signal to probe 14. Upon receipt of the trigger signal, the probe 14 transmits an acoustic energy search signal into the workpiece and receives entrant surface and defect responsive echo signals therfrom. The echo responsive signals are conducted to receiver 16 from which the echo responsive electrical signals are conducted to the comparator 18 and the measuring clock 20. Defects occurring during the defect gate time interval are provided along conductor 25 for further evaluation.

When testing a workpiece having an unknown acoustic velocity, the workpiece is acoustically coupled to a workpiece of known thickness. A cathode ray tube is coupled in circuit for simultaneously displaying the echo responsive electrical signals from receiver 16 and the defect gate from gate generator circuit 26. Address 90 is set to zero for causing the defect gate to commence upon receipt of the entrant surface responsive electrical signal. Address 92 is then set to the known workpiece thickness. The operator observes on the cathode ray tube the end of the defect gate and the receipt of the rear wall responsive electrical signal. The address 62 is adjusted until the rear wall responsive electrical signal is received at precisely the time the defect gate ends. Upon the simultaneous occurrence of these two events, the address means 62 is adjusted to the acoustic velocity of the workpiece. After the address means 62 is properly adjusted, addresses 90 and 92 are set for the desired workpiece region and defect testing commences.

It will be understood that upon any drift of the oscillator 34 frequency, the cllock 20 readjusts the oscillator 34 frequency each time a trigger pulse is manifest at the output of clock 10, as described above. Hence the present invention provides a clock exhibiting long term stability by virtue of a frequency check being performed every time an ultrasonic energy search pulse is transmitted into the workpiece.

In a modification of the embodiment per FIG. 4, especially when using pulse-echo ultrasonic contact testing, the monostable multivibrator 50 may be commenced responsive to the trigger pulse from clock 10 instead of being responsive to an entrant surface echo responsive signal.

It will also be apparent that the clock pulses from measuring clock 20 may also be used to accurately determine the distance from the entrant surface to an acoustic discontinuity in the workpiece by counting the quantity of clock pulses received after transmission of a trigger pulse until receipt of an echo responsive electrical signal.

While a preferred embodiment of the invention and several modifications thereof have been described and illustrated, it will be apparent to those skilled in the art that additional changes and modifications may be made therein without deviating from the broad principle and spirit of the invention which shall be limited solely by the scope of the appended claims.

What is claimed is:

1. A long term stable, programmable clock circuit for use in a pulse-echo ultrasonic apparatus comprising:
   a synchronizable voltage controlled oscillator for providing clock pulses;
   gated counting means coupled to said oscillator for counting during a predetermined time interval the quantity of said clock pulses and providing a count signal responsive to said quantity;
   address means for providing a predetermined count signal;
   comparator means coupled to said gated counting means and said address means for comparing said count signal and said predetermined count signal and providing an output signal indicative of a difference between said count signal and said predetermined count signal;
   counter means coupled to said comparator means for receiving said output signal and providing a difference count signal, and
   means coupled to said counter means and said oscillator for receiving said difference count signal and providing a feedback signal to said oscillator for causing said count signal to be substantially equal to said predetermined count signal.

2. A clock circuit as set forth in claim 1, said oscillator comprising:
   an adjustable ramp generator for providing ramp waveform voltage signals responsive to said feedback signal;
   a voltage source for providing a predetermined voltage signal;
   means for providing enabling pulses, and
   comparison means coupled for receiving said ramp waveform voltage signals, said predetermined voltage signal, and said enabling pulses for providing said clock pulses having a frequency responsive to said ramp waveform voltage signals.

3. A clock circuit as set forth in claim 2, said means for providing enabling pulses being enabled by a synchronizing signal for synchronizing said clock pulses to said synchronizing signal.

4. A clock circuit as set forth in claim 1, said means coupled to said counter means being a digital to analog converter.

* * * * *